(12) United States Patent
Yun et al.

(10) Patent No.: US 9,068,188 B2
(45) Date of Patent: Jun. 30, 2015

(54) PROMOTER OF CORYNEBACTERIA

(71) Applicant: Samsung Electronics Co., Ltd., Suwon-si, Gyeonggi-do (KR)

(72) Inventors: Ji-ae Yun, Seoul (KR); Joon-song Park, Seoul (KR); Woo-yong Lee, Hwaseong-si (KR); Jae-chan Park, Yongin-si (KR); Jin-hwan Park, Suwon-si (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 0 days.

(21) Appl. No.: 14/088,111

(22) Filed: Nov. 22, 2013

(65) Prior Publication Data

US 2014/0147889 A1    May 29, 2014

(30) Foreign Application Priority Data

Nov. 23, 2012 (KR) .................. 10-2012-0133940

(51) Int. Cl.
*C12N 15/77* (2006.01)
*C07K 14/34* (2006.01)

(52) U.S. Cl.
CPC ............. *C12N 15/77* (2013.01); *C07K 14/34* (2013.01)

(58) Field of Classification Search
None
See application file for complete search history.

(56) References Cited

U.S. PATENT DOCUMENTS

| 7,763,447 | B2 | 7/2010 | Murase et al. |
| 7,993,888 | B2 | 8/2011 | Murase et al. |
| 2006/0205048 | A1 | 9/2006 | Murase et al. |
| 2007/0231867 | A1 | 10/2007 | Choi et al. |
| 2008/0166775 | A1 | 7/2008 | Kroger et al. |
| 2008/0171371 | A1 | 7/2008 | Yukawa et al. |
| 2009/0156779 | A1 | 6/2009 | Murase et al. |
| 2010/0261256 | A1 | 10/2010 | Rah et al. |
| 2011/0076731 | A1 | 3/2011 | Kim et al. |

OTHER PUBLICATIONS

Ikeda et al., "The *Corynebacterium glutamicum* genome: features and impacts on biotechnological processes," *Applied Microbiology and Biotechnology* 62: 99-109 (2003).
Park et al., "Isolation and Characterization of Transcriptional Elements from *Corynebacterium glutamicum*," *Journal of Microbiology and Biotechnology* 14(4): 789-795 (2004).
Pátek et al., "Promoters from *Corynebacterium glutamicum*: cloning, molecular analysis and search for a consensus motif," *Microbiology* 142: 1297-1309 (1996).
Pátek et al., "Promoters of *Corynebacterium glutamicum*," *Journal of Biotechnology* 104: 311-323 (2003).
Pátek et al., "Sigma factors and promoters in *Corynebacterium glutamicum*," *Journal of Biotechnology* 154: 101-113 (2011).
Vašicová et al., "Analysis of the *Corynebacterium glutamicum dapA* Promoter," *Journal of Bacteriology* 181(19): 6188-6191 (Oct. 1999).

*Primary Examiner* — Michele K Joike
*Assistant Examiner* — Mindy G Brown
(74) *Attorney, Agent, or Firm* — Leydig, Voit & Mayer, Ltd.

(57) ABSTRACT

An isolated nucleic acid comprising a promoter region having a nucleotide sequence of SEQ ID NO: 1, which can maintain high expression under aerobic and anaerobic conditions, and related compositions and methods.

11 Claims, 2 Drawing Sheets

PROMOTER OF CORYNEBACTERIA

CROSS-REFERENCE TO RELATED APPLICATIONS

This application claims the benefit of Korean Patent Application No. 10-2012-0133940, filed on Nov. 23, 2012, in the Korean Intellectual Property Office, the disclosure of which is incorporated herein in its entirety by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 2,834 Byte ASCII (Text) file named "712661_ST25.TXT," created on Sep. 3, 2013.

BACKGROUND

1. Field

The present disclosure relates to a novel promoter of Corynebacteria, a vector including the promoter, a host cell comprising the vector, and a method of expressing a gene using the host cell.

2. Description of the Related Art

Species of the genus Corynebacterium, or corynebacteria, particularly Corynebacterium glutamicum, is a gram-positive bacteria which is used to produce amino acids, such as glutamate, lysine, and threonine. Corynebacterium glutamicum grows under relatively simple culture conditions, may be cultured at a high concentration compared to Escherichia coli, and has a stable genetic structure, thus having a low possibility of mutation occurrence. Also, since Corynebacterium glutamicum is nonpathogenic and does not produce spores, the strain does not have a malignant influence on the environment and, thus, may be used as an industrial strain.

Corynebacterium glutamicum is an aerobe, and its growth is ceased under anaerobic conditions or when oxygen supply is stopped. Under anaerobic conditions, metabolic processes of Corynebacterium glutamicum other than those necessary in producing minimum energy for survival are ceased, and lactic acid, acetic acid, succinic acid etc. are produced and released from Corynebacterium glutamicum. In this regard, metabolism of Corynebacterium glutamicum is focused on producing and releasing the desired products under anaerobic conditions, and growth may be less of a concern, and, thus, bacteria may be maintained at a high concentration.

A promoter is a DNA region to which an RNA polymerase binds to initiate the transcription of a gene which is operably linked to the promoter. The strength and conditions of the gene expression are determined, at least in part, by the promoter sequences and/or length of the promoter, whether RNA polymerase and transcription factors bind the promoter sequences, and the strength of the binding. The transcription factors include modulator proteins, by which gene expressions are modulated only under particular environmental conditions, such as growth state of cells, oxygen requirement, and temperature.

Industrial application of microorganisms is often based on the overexpression of desired genes. In the case of prokaryotes, most genes may be overexpressed when a strong promoter is used, and thus it is important to search for a strong promoter that may be well expressed under given production conditions. In particular, although Corynebacteria have long been used as industrial microorganisms, studies on anaerobic fermentation of Corynebacteria have only just begun. Thus, finding a promoter that functions at a satisfactory level under anaerobic conditions is necessary.

SUMMARY

Provided is an isolated recombinant nucleic acid comprising a promoter region with a nucleotide sequence of SEQ ID NO: 1, as well as a vector comprising the promoter nucleic acid sequence.

Provided is a host cell comprising the isolated nucleic acid or vector, optionally including a target gene that is operably linked to a nucleic acid sequence (promoter) comprising the nucleotide sequence of SEQ ID NO: 1.

Provided is a method of expressing a target gene, the method including culturing the host cell.

Additional aspects will be set forth in part in the description which follows and, in part, will be apparent from the description, or may be learned by practice of the presented embodiments.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
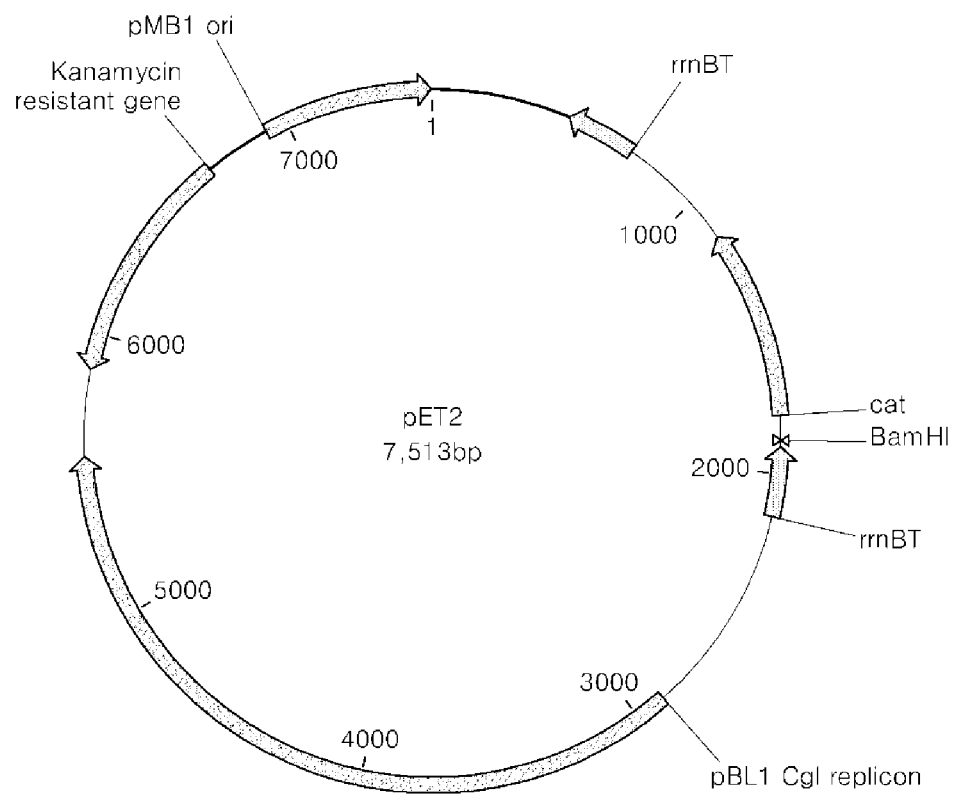
FIG. 1 shows a vector that is used for screening a promoter.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description.

According to an aspect of the present invention, there is provided an isolated recombinant nucleic acid comprising a promoter region with a nucleotide sequence of SEQ ID NO: 1. The isolated nucleic acid can comprise, consisting essentially of, or consisting of the nucleotide sequence of SEQ ID NO: 1. The term "promoter" used herein indicates a DNA region to which an RNA polymerase binds to initiate the transcription of a nucleic acid sequence (e.g., a gene) which is operably linked to the promoter. The sequence of the promoter may be modified within a range of the same or similar activities by one of ordinary skill in the art. Thus, an aspect of the present invention includes an isolated nucleic acid sequence (promoter) having a sequence identity or homology of, for example, at least 70%, at least 80%, at least 90%, or at least 95% to the nucleotide sequence of SEQ ID NO: 1. The promoter may also be another nucleotide fragment (hereinafter, referred to as "variant") comprising particular portions of SEQ ID NO: 1 that are essential for the promoter activity, for example, sequences (hereinafter, referred to as "variant") of a transcription start site and −10 element. The positions of the transcription start site and −10 elements are provided in Example 1.

According to another aspect of the present invention, there is provided a vector comprising, consisting essentially of, or consisting of the above-described nucleic acid sequence (e.g., a promoter having a sequence of SEQ ID NO: 1 or a variant of the promoter). The vector may include a target nucleic acid sequence (e.g., gene) that is operably linked to the promoter or a variant thereof. The term "operably linked" used herein indicates that a gene to be expressed is functionally linked to its control sequences so that the gene is properly expressed. The gene may be involved in production of useful metabolites, for example, intermediates of TCA cycle or metabolites derived from the intermediates. The vector may further include a replication origin, a promoter control site, a ribosome binding site, a transcription terminal site, a screening marker, or a combination thereof, as well as the target gene and the promoter or its variant.

In the vector, the gene operably linked to the promoter or its variant may be expressed, for example, under anaerobic conditions. For example, the gene may be highly expressed under aerobic conditions and may also maintain a relatively high level of gene expression under anaerobic conditions. Under aerobic conditions, an amount of gene expression may be 4 times or more, for example, 5 times or more, 6 times or more, or 7 times or more, than an amount of expression of the gene which is operably linked to a glyceraldehydes-3-phosphate dehydrogenase A (gapA) promoter based on an amount of mRNA of the gene operably linked to the promoter. Under anaerobic conditions, an amount of gene expression may be 1.2 times or more, for example, 1.5 times or more, 2 times or more, or 2.5 times or more, than an amount of expression of the gene which is operably linked to a gapA promoter based on an amount of mRNA of the gene operably linked to the promoter.

According to another aspect of the present invention, there is provided a host cell having a recombinant nucleic acid including a promoter region comprising a nucleotide sequence of SEQ ID NO: 1 or a variant thereof. The recombinant nucleic acid may be integrated into a chromosome of the host cell or the recombinant nucleic acid may be in the form of a vector in the host cell. In the chromosome or the vector, a target gene may operably be linked to a promoter having a nucleotide sequence of SEQ ID NO: 1 or a variant of the promoter. The host cell may be, for example, a strain in *Escherichia coli* or *Corynebacterium*. The strain may be, for example, *Corynebacterium glutamicum*, *Corynebacterium thermoaminogenes*, *Brevibacterium flavum*, or *Brevibacterium lactofermentum*. In one embodiment, the strain may be, for example, *Corynebacterium glutamicum* ATCC 13032.

The vector may be introduced to the host cell, for example, to clone the target gene. The vector may also be introduced to the host cell, for example, to express the target gene. The introduction of the vector may be performed by applying appropriate standard techniques known in the art, depending on the host cell. For example, the introduction of the vector may be performed using electroporation, heat-shock, or a combination thereof.

The vector introduced to the host cell may include a nucleic acid sequence (e.g., gene), which is involved in production of useful metabolites, for example, intermediates of TCA cycle or metabolites derived from the intermediates, operably linked downstream of the promoter or a variant thereof. The vector may further include a replication origin, a promoter control site, a ribosome binding site, a transcription terminal site, a screening marker, or a combination thereof, as well as the target gene and the promoter or its variant. The host cell may express the gene operably linked to the promoter or its variant, for example, under anaerobic conditions. For example, the gene may be highly expressed under aerobic conditions and may also maintain a relatively high level of gene expression under anaerobic conditions. Under aerobic conditions, an amount of gene expression may be 4 times or more, for example, 5 times or more, 6 times or more, or 7 times or more, than an amount of expression of the gene which is operably linked to a glyceraldehydes-3-phosphate dehydrogenase A (gapA) promoter based on an amount of mRNA of the gene operably linked to the promoter. Under anaerobic conditions, the amount of gene expression may be 1.2 times or more, for example, 1.5 times or more, 2 times or more, or 2.5 times or more, than an amount of expression of the gene which is operably linked to a gapA promoter based on an amount of mRNA of the gene operably linked to the promoter.

According to another aspect of the present invention, there is provided a method of expressing a target nucleic acid sequence (e.g., target gene), where the method includes culturing the host cell having a vector comprising, consisting essentially of, or consisting of the above-described nucleic acid sequence (e.g., a promoter having a sequence of SEQ ID NO: 1 or a variant of the promoter) to which a target gene is operably linked. The method of expressing the target gene may be, for example, a method to produce a final product of a biosynthetic pathway, wherein a protein that is encoded by the target gene is involved in the pathway, by culturing the host cell in which the vector is introduced. The target gene may be involved in production of useful metabolites, for example, intermediates of TCA cycle or metabolites derived from the intermediates. The method may produce the product of the target gene, for example, under anaerobic conditions. The product of the method may be, for example, produced in massive amounts under aerobic conditions and may maintain a relatively high level of production under anaerobic conditions. Under aerobic conditions, an amount of gene expression may be 4 times or more, for example, 5 times or more, 6 times or more, or 7 times or more, than an amount of expression of the gene which is operably linked to a gapA promoter based on an amount of mRNA of the gene operably linked to the promoter. Under anaerobic conditions, the amount of gene expression may be 1.2 times or more, for example, 1.5 times or more, 2 times or more, or 2.5 times or more, than an amount of expression of the gene which is operably linked to a gapA promoter based on an amount of mRNA of the gene operably linked to the promoter. The host cell may be, for example, *Corynebacterium glutamicum* in which a vector is introduced, wherein the vector includes the gene involved in production of the product, wherein the gene involved in production of the product is operably linked either to the promoter having the nucleotide sequence of SEQ ID NO: 1 or to the variant of the promoter.

The culturing of the host cell may be performed according to methods that are known in the art. Culture medium used for the culturing may include, for example, sugar and a carbohydrate (e.g., glucose, sucrose, lactose, fructose, maltose, starch, and cellulose), oil and fat (e.g., soybean oil, sunflower oil, castor oil, and coconut oil), a fatty acid (e.g., palmitic acid, stearic acid, and linolenic acid), an alcohol (e.g., glycerol and ethanol), and an organic acid (e.g., acetic acid) as a carbon source. The carbon source may be used alone or in a mixture.

The culture medium may include, for example, a nitrogen-containing organic compound (e.g., tryptone, peptone, yeast extract, meat extract, malt extract, corn steep liquor, soy meal and urea) or an inorganic compound (e.g., ammonium sulfate, ammonium chloride, ammonium phosphate, ammonium carbonate and ammonium nitrate) as a nitrogen source. The nitrogen source may be used alone or in a mixture.

The culture medium may include, for example, potassium dihydrogen phosphate, dipotassium hydrogen phosphate or its sodium salt thereof as a phosphorous source. The culture medium may include a metal salt (e.g., magnesium sulfate or iron sulfate) essential for growth. Also, the culture medium may further include substances essential for growth, such as amino acids and vitamins, or suitable precursors.

Those components of culture media may be added to the culture media, for example, in a batch or on a continuous basis during the culturing.

The present invention will be described in further detail with reference to the following examples. These examples are for illustrative purposes only and are not intended to limit the scope of the present invention.

EXAMPLE 1

Construction of Promoter Library

Genomic DNA was extracted from a *Corynebacterium glutamicum* ATCC 13032 strain and partially cleaved with Sau3AI. DNA fragments having a size of about 0.5 to about 1.5 kb in the cleaved products were extracted from 1% agarose gel. Each of the extracted DNA fragments was cloned into pET2 vector treated with BamHI (see FIG. 1), transformed into *E. coli* Top 10 competent cells (Invitrogen), and the cells were spread on LB solid medium containing kanamycin (50 µg/ml) and chloramphenicol (10 µg/ml). Then, plasmids were isolated from pooled colonies, transformed into *Corynebacterium glutamicum* ATCC 13032, and the cells were spread on LB solid medium containing kanamycin (25 µg/ml) to obtain colonies.

EXAMPLE 2

Screening promoter and selecting P33

The colonies of *Corynebacterium glutamicum* obtained in Example 1 were inoculated into, and cultured in, LB liquid medium containing kanamycin (25 µg/ml) in 96-wells until they reached late-log phase. Then each culture was reinoculated into, and cultured in, the LB liquid medium containing kanamycin (25 µg/ml) and chloramphenicol (80 µg/ml) at 30° C. at 220 rpm for 24 hours or longer. Plasmids were isolated from cultures with the OD 600 value of 0.2 or higher, and sequenced using primers below.

TABLE 1

| Primer | Sequence (SEQ ID NO) |
|---|---|
| pET2_SeqR | ATG TTC TTT ACG ATG CCA TTG GGA (SEQ ID NO: 2) |
| pET2_SeqF | TCT CCT GAG TAG GAC AAA TCC G (SEQ ID NO: 3) |

As a result of the sequencing, the DNA cloned into the BamHI site of the pET2 vector corresponded to an upper region of NCgl 0333 (SEQ ID NO: 1), which has not been known for its function, of *Corynebacterium glutamicum* ATCC 13032. This promoter sequence was named P33. The transcription start site of P33 was predicted using a promoter prediction program, Neural Network Promoter Prediction. The −10 region predicted in SEQ ID NO: 1 is TATTCT', which corresponds to the $885^{th}$ to $890^{th}$ residues of SEQ ID NO: 1, and a transcription start site is 'C', which is the $896^{th}$ residue of SEQ ID NO: 1.

EXAMPLE 3

Verification of Promoter Strength

*Corynebacterium glutamicum* having a recombinant pET2 vector including the P33 promoter was inoculated into LB broth containing 2% glucose. The medium was then cultured under aerobic conditions for about 12 hours, and then the medium was transferred and cultured under anaerobic conditions for about 24 hours. RNA was extracted from the culture using RNeasy® Mini kit (Qiagen) under both aerobic and anaerobic conditions. 1 µg of the extracted RNA was reverse transcribed into cDNA using Superscript® VILO™ cDNA Synthesis kit (Invitrogen), and then the primers below were used to confirm an amount of cDNA of the target gene (chloramphenicol acetyl transferase) operably linked to the promoter by real-time PCR. LightCycler® 480 Real-Time System (Roche) was used, and a mixture including 2 µl of cDNA, 10 µl of LightCycler® 480 SYBR Green I Master, the primers listed below (0.5 µl and 10 µM, respectively), and 7 µl of distilled water was pre-heated at a temperature of about 95° C. for about 10 minutes, and then repeatedly heated at about 95° C. for about 30 seconds and at about 60° C. for about 30 seconds for 45 times. An amount of cDNA of chloramphenicol acetyl transferase (cat) was calculated by calculating $2^{-\Delta\Delta ct}$ value.

TABLE 2

| Primer | Sequence (SEQ ID NO) |
|---|---|
| catF | TGCTCATGGAAAACGGTGTA (SEQ ID NO: 4) |
| catR | TCCGGCCTTTATTCACATTC (SEQ ID NO: 5) |

Figure 2:
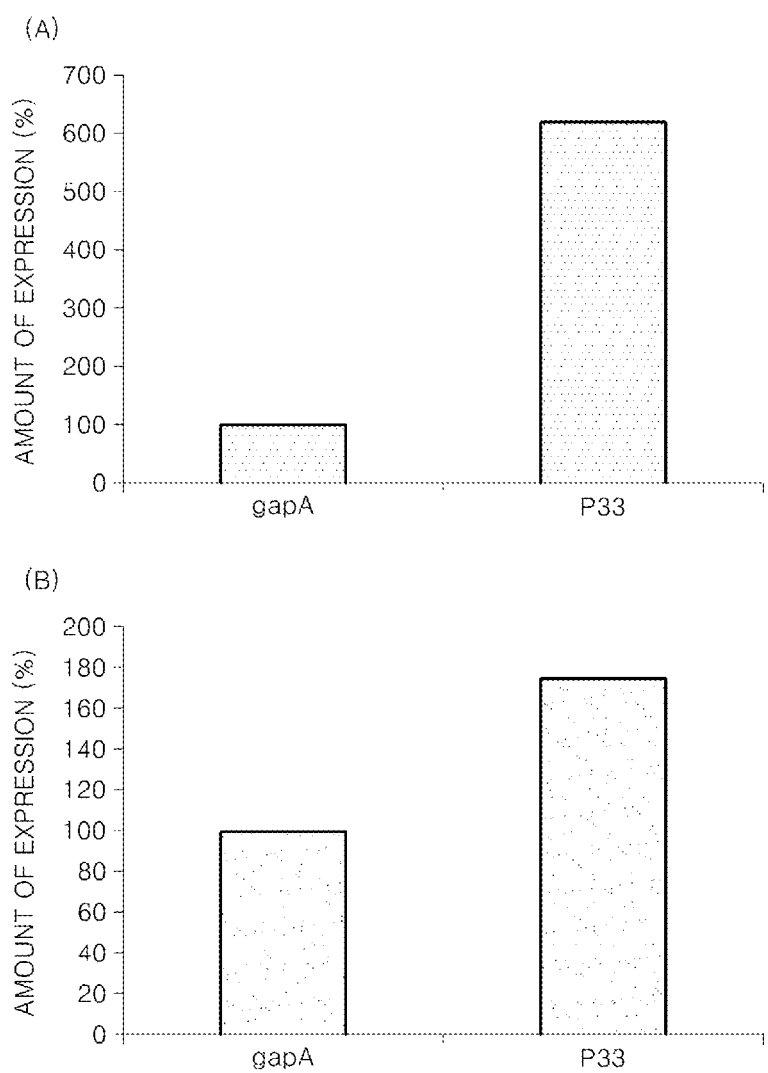
FIGS. 2A and 2B are graphs comparing the activity of P33 promoter and gapA promoter under (A) aerobic or (B) anaerobic conditions. The amount of gene expression (%) of target gene (chloramphenicol acetyl transferase) operably linked to the respective promoters is indicated on the y-axis.

A recombinant pET2 vector where gapA promoter (SEQ ID NO: 6) was cloned into a BamHI site was used as a control group. The strength of the P33 promoter under aerobic conditions or anaerobic conditions was compared with the strength of the gapA promoter, and the results are shown in Table 3 and FIG. 2. Activity of the P33 promoter appeared to be stronger by 6 times or more than the gapA promoter under aerobic conditions, and by 1.7 times or more under anaerobic conditions.

TABLE 3

| Conditions | gapA promoter | P33 promoter |
|---|---|---|
| Aerobic | 100% | 620% |
| Anaerobic | 100% | 175% |

As described above, according to the one or more of the above embodiments of the present invention, a promoter, a vector including the promoter, a host cell having the vector, and a method of expressing a gene by using the host cell may be used to over-express a target gene from *Corynebacterium* under anaerobic conditions as well as aerobic conditions.

It should be understood that the exemplary embodiments described therein should be considered in a descriptive sense only and not for purposes of limitation. Descriptions of features or aspects within each embodiment should typically be considered as available for other similar features or aspects in other embodiments.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. An isolated recombinant nucleic acid comprising a promoter region having the nucleotide sequence of SEQ ID NO: 1.

2. The isolated recombinant nucleic acid of claim 1, wherein the isolated recombinant nucleic acid is a vector.

3. The isolated recombinant nucleic acid of claim 1, wherein a target gene is operably linked to the promoter region.

4. A host cell comprising a recombinant nucleic acid comprising a promoter region having the nucleotide sequence of SEQ ID NO: 1.

5. The host cell of claim 4, wherein the recombinant nucleic acid is a vector.

6. The host cell of claim 4, wherein a target gene is operably linked to the promoter region.

7. The host cell of claim 4, wherein the host cell is *Corynebacterium glutamicum*.

8. A method of expressing a target gene, the method comprising culturing a host cell comprising a recombinant nucleic acid comprising a promoter region having the nucleotide sequence of SEQ ID NO: 1 and a target gene operably linked to the promoter region, thereby expressing the target gene.

9. The method of claim 8, wherein the host cell is *Corynebacterium glutamicum*.

10. The method of claim 9, wherein the host cell is cultured under anaerobic conditions.

11. The method of claim 10, wherein expression of the target gene operably linked to the promoter region is greater than expression of the same gene is operably linked to a gapA promoter under the same conditions.

* * * * *

SEQUENCE LISTING

```
<160> NUMBER OF SEQ ID NOS: 6

<210> SEQ ID NO 1
<211> LENGTH: 1019
<212> TYPE: DNA
<213> ORGANISM: Artificial Sequence
<220> FEATURE:
<223> OTHER INFORMATION: Synthetic (Corynebacterum glutamicum)

<400> SEQUENCE: 1
atgattggca tgcgtaaaac cctcatcacc atgctcgcga ccaccgcgat cgccttttcc      60
gccatctcac cagtgcaggc gcaaaccgtg gacacagaca ctgacgcctc cgtgtcatct     120
gagctgagca gcggcacaag ctcaggaagt tcagaggatt ccgaagattc tgacatctcc     180
aaccgggaca tcatcttcgg catcgcagct atcgctgcag tcggcggact tatcgcaagt     240
ggtgtgcact gggcagtaca acagcgcatg atcccaaatc ccctcccagg aatcattcca     300
aatccccctg cactggcacc tcaggcgcct gccccagcac ctgctcccgc tcctgcccct     360
caggcagtcg cgccccaggt tgtcgctccc caggttgtcg cgcctgctcc agccccagta     420
cagaccaacc gcacctacaa aaactgcacc gaagtatgga acgtcctggg aaggtccatc     480
cgccaaagcg atccaggcta cggcacacac ctcgaccgcg accgcgacgg catcggctgc     540
gaatcacgcc ctaggtagtt tgggttttgg ggatcttcgg gagttgctaa gactcttagg     600
gcctcggagg tcatgagtcc cttgatctaa gccttttaag gcggtgagtt gagtaaactc     660
accgcctcat atgtaatttt aagctgccta tccgtagagt ctggcttgca aagagactat     720
cgctctactt ggggcaccgc attcatcaaa acaattaact gcccaaagta taagaaatcg     780
ggtacacaaa accaccgaca cagaagagtc catcccgcga tgcggggagc gctcctttag     840
gggctcttca ttgcagactt gtgaccagcc gaatctacat tccttattct gctggcgtta     900
caattcaggg ccaaacccgt atgatgaaaa agacaccggg gaaatcggag tgcgcgtaga     960
ttttgaaaac ggccggtact actcggttca cgtttacgtc ggctgatcca attggaggg    1019

<210> SEQ ID NO 2
```

```
<211> LENGTH: 24
<212> TYPE: DNA
<213> ORGANISM: Artificial Sequence
<220> FEATURE:
<223> OTHER INFORMATION: Synthetic (pET2_SeqR)

<400> SEQUENCE: 2 atgttctttta cgatgccatt ggga                                          24

<210> SEQ ID NO 3
<211> LENGTH: 22
<212> TYPE: DNA
<213> ORGANISM: Artificial Sequence
<220> FEATURE:
<223> OTHER INFORMATION: Synthetic (pET2_SeqF)

<400> SEQUENCE: 3
tctcctgagt aggacaaatc cg                                             22

<210> SEQ ID NO 4
<211> LENGTH: 20
<212> TYPE: DNA
<213> ORGANISM: Artificial Sequence
<220> FEATURE:
<223> OTHER INFORMATION: Synthetic (catF)

<400> SEQUENCE: 4
tgctcatgga aaacggtgta                                                20

<210> SEQ ID NO 5
<211> LENGTH: 20
<212> TYPE: DNA
<213> ORGANISM: Artificial Sequence
<220> FEATURE:
<223> OTHER INFORMATION: Synthetic (catR)

<400> SEQUENCE: 5
tccggccttt attcacattc                                                20

<210> SEQ ID NO 6
<211> LENGTH: 237
<212> TYPE: DNA
<213> ORGANISM: Escherichia coli

<400> SEQUENCE: 6
atgattttgc atctgctgcg aaatctttgt ttccccgcta agttgagga caggttgaca      60 cggagttgac tcgacgaatt atccaatgtg agtaggtttg gtgcgtgagt tggaaaaatt    120
cgccatactc gcccttgggt tctgtcagct caagaattct tgagtgaccg atgctctgat    180
tgacctaact gcttgacaca ttgcatttcc tacaatcttt agaggagaca caacatg      237
```